United States Patent [19]

Wei

[11] 4,039,428
[45] Aug. 2, 1977

[54] PURIFICATION OF PROPIONIC ACID

[75] Inventor: YuWen Wei, Houston, Tex.

[73] Assignee: Monsanto Company, St. Louis, Mo.

[21] Appl. No.: 646,291

[22] Filed: Jan. 2, 1976

[51] Int. Cl.$^2$ .......................... B01D 3/32; C07C 51/44
[52] U.S. Cl. ........................................ 203/37; 203/15;
  203/33; 203/36; 203/38; 203/41; 203/DIG. 19;
  260/540
[58] Field of Search ....................... 203/15, 16, 28, 29,
  203/38, 39, 41, 99, DIG. 19, 33, 36, 37;
  260/540, 541, 542

[56] References Cited

U.S. PATENT DOCUMENTS

| | | | |
|---|---|---|---|
| 3,084,109 | 4/1963 | Ure et al. | 203/37 |
| 3,439,026 | 4/1969 | Patton et al. | 260/540 |
| 3,490,997 | 1/1970 | Burney et al. | 203/37 |
| 3,530,043 | 9/1970 | Horn et al. | 203/33 |
| 3,769,177 | 10/1973 | Eubanks et al. | 203/16 |
| 3,772,156 | 11/1973 | Johnson et al. | 203/37 |
| 3,791,935 | 2/1974 | Eubanks et al. | 203/16 |

Primary Examiner—Wilbur L. Bascomb, Jr.
Attorney, Agent, or Firm—Elizabeth F. Sporar

[57] ABSTRACT

A process is provided for producing ultra-pure propionic acid, i.e., acid containing less than 20 parts by weight of iodine per billion parts by weight of acid, wherein crude acid containing water and iodine contaminants is distilled in a single distillation zone and no waste streams requiring treatment or disposal are obtained.

10 Claims, 1 Drawing Figure

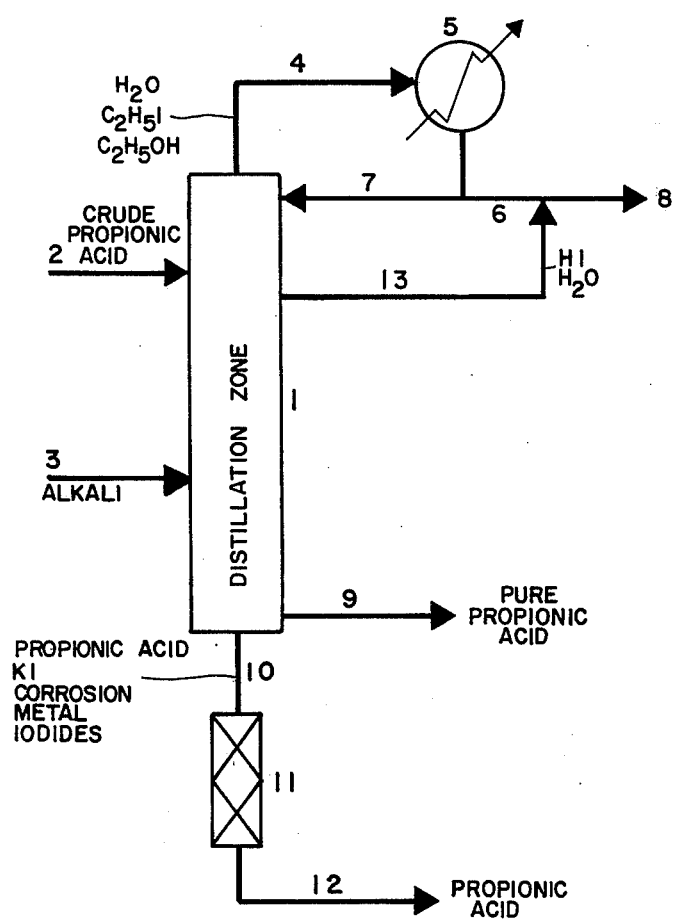

PURIFICATION OF PROPIONIC ACID

BACKGROUND OF THE INVENTION

The present invention relates to the purification of propionic acid. More particularly, it relates to a method for the purification of a stream of propionic acid containing water and iodine as impurities.

Propionic acid can be prepared by the reaction of ethylene, water and carbon monoxide or of ethanol and carbon monoxide using catalyst systems formed on mixing of a rhodium or iridium component and an iodine component in the presence of carbon monoxide. See, for example, U.S. Pat. Nos. 3,579,551, 3,579,552, 3,769,329 and 3,772,380. Hydrogen iodide or an alkyl iodide, namely, ethyl iodide, is usually employed as the iodine component in these catalyst systems. While the acid produced by this process is generally of high purity, it sometimes contains residual amounts of iodine either as ionic iodine, free iodine or as ethyl iodide. Such contaminants may render the acid unfit for some uses. In some instances, it may become desirable to produce ultra-pure propionic acid, i.e., acid having an iodine content, as measured by ethyl iodide and ionic iodide (I-), below a level of 20 parts per billion parts of acid (20 ppb). Distillation techniques are known by which such ultra-pure acids can be obtained but these generally require two or more columns. An example of one such type of distillation is to be found in U.S. Pat. No. 3,772,156, for example, wherein a process for producing an acetic acid product containing less than 40 ppb of iodine is described and claimed. It is an object of the present invention to provide a one-column distillation system wherein crude propionic acid can be converted to ultra-pure propionic acid. Additionally, it is an object of the invention to provide a process to produce ultra-pure propionic acid from ethylene or ethanol without a single waste stream requiring treatment or disposal. Other objects and advantages of the invention will become apparent from the following description thereof.

SUMMARY OF THE INVENTION

According to the present invention, a stream of propionic acid containing water and iodine either as I-, free iodine, or ethyl iodide, or all of these, is introduced into the upper section of a distillation zone, an alkaline compound which is a compound of an alkali metal or an alkaline earth metal is introduced into the lower section of said distillation zone, a stream is removed overhead from said distillation zone containing the major proportion of the water present along with substantially all the ethyl iodide, a part of said stream is returned as reflux to said distillation zone whereas the remainder is stored or recycled to the acid-producing step, a stream containing substantially all the hydrogen iodide present along with the remaining portion of the water is removed as a liquid sidestream from the upper section of said distillation zone, a product propionic acid stream essentially dry and containing less than 20 ppb iodine is withdrawn as a vapor near the bottom of said distillation zone, and a stream containing propionic acid, corrosion metal iodides and potassium iodide is removed from the bottom of the column, passed through a cation exchange resin bed and recovered for recycle to the acid-producing step.

BRIEF DESCRIPTION OF THE DRAWING

FIG. 1 is a schematic flow diagram of the purification process of the present invention.

DESCRIPTION OF THE PREFERRED EMBODIMENT

Reference is now made to FIG. 1 for a description of how the purification process of the present invention is carried out. A crude propionic acid product containing water, hydrogen iodide, ethanol, ethyl iodide, ethyl propionate and propionic acid is introduced into distillation zone 1 via line 2. Into the lower section of the column via line 3, there is introduced a stream of an alkaline compound such as potassium hydroxide, for example. A stream is removed overhead from the column via line 4 containing the major portion of the water present in the column, substantially all of the ethyl iodide, ethanol, and ethyl propionate, is condensed in condenser 5, the main portion thereof being withdrawn via line 6 while the remainder is returned to the column as reflux via line 7. Hydrogen iodide and the remainder of the water are removed as a liquid sidedraw via line 13 and combined with the condensate in line 6 to form stream 8 which is withdrawn for storage or recycle to the acid-producing step. An ultra-pure propionic acid product containing 20 ppb or less of I- and 1 ppb ethyl iodide is withdrawn as a vapor via line 9, condensed and sent to storage facilities. A stream containing propionic acid, potassium iodide and corrosion metal iodides is withdrawn from the bottom of the column via line 10 and introduced into the ion exchange column 11 packed with a cation exchange resin through which the stream passes. In the exchange column, the metals in the acid solution are removed and the effluent from the column consisting essentially of propionic acid removed via line 12 is suitable for recycle to the acid-producing step.

Any type distillation column normally used for separation and purification can be employed in the process of the invention. The column can be either the packed- or plate-type or a combination of the packed-plate type. Generally, the column will be a plate-type column having from 20 to 80 and preferably 30 to 60 theoretical trays. In the preferred embodiment, sieve trays are employed although other type trays such as bubble-cap and ballast may be used.

The temperatures and pressures employed in the column may vary. Usual pressures for operation are those from approximately atmospheric to about 50 psig although subatmospheric or superatmospheric pressures may be employed if desired. Preferably, however, the distillation column is usually operated at a pressure within the range of 0 to 25 psig.

Temperature within the column will normally be between the boiling point of the propionic acid being purified at the pressure of the column and the temperature at which the propionic acid-water azeotrope boils at the pressure of the column. At the preferred pressures the bottoms temperature generally will be at the boiling point of the acid at the pressure employed. The crude acid feed is introduced at a temperature around about 110° C and the overhead temperature is maintained within one or two degrees of the boiling point of water depending upon the column pressure.

While the point of introduction of the feed stream can vary, this stream is preferably introduced into the upper section of the column and preferably into the top one-third thereof.

The alkaline compound is introduced into the lower half of the column preferably into the lower third thereof and even more desirably into the lower one-tenth of the column. Suitable alkaline compounds for use in the practice of the purification process of the invention includes the oxides, hydroxides, carbonates, bicarbonates and salts of weak organic acids of both the alkali metals, in general, such as potassium, sodium, rubidium and cesium and the alkaline earth metals such as calcium, barium and strontium. The acetates are the particularly preferred compounds although the hydroxides represent more economical operation. When the hydroxides are employed, care should be taken to see that the chloride level in these materials, as for example, in sodium hydroxide, is less than one percent to avoid occurrence of any corrosion problems. Potassium compounds are preferred for use as the treating agents.

The amount of alkaline compound to be added is an amount in stoichiometric excess of the amount of ionic iodine and free iodine present in the lower third of the distillation zone. Preferably, in view of the minute quantities of impurities being removed, a 100-fold excess is employed. Generally, amounts from about $50 \times 10^{-6}$ to about $500 \times 10^{-6}$ parts by weight per part by weight of acid product are employed and preferably the amount used is from about $200 \times 10^{-6}$ to about $300 \times 10^{-6}$ parts by weight per part by weight of acid product. As a matter of convenience, the alkaline compound can be introduced as an aqueous solution of about 25–75% concentration when the hydroxide is employed, or when the salts are used, an aqueous solution of about 50% concentration, although any desired concentration can be used. Also, a solution of the alkaline compound in propionic acid can be employed if desired.

The percentage of the feed to the distillation zone removed as an overhead fraction from said zone can vary somewhat. Generally, the overhead stream will range from about 30% to about 70% by weight and preferably from 50 to 65% by weight of the total feed. The column reflux can be varied as desired but is generally maintained from about 2:1 to about 5:1.

Hydrogen iodide and the water not removed overhead from the column are removed via the liquid sidestream 13 which generally constitutes from about 4% to about 10% by weight of the total feed to the column. Preferably, this stream constitutes about 6% of the total feed. This sidestream is usually removed from the upper part of the column at a point at or near the peak of hydrogen iodide concentration which is generally in the upper one-third of the column either slightly above or slightly below the point of introduction of the feed. This stream as has been indicated previously can be joined with the overhead stream and treated in a like manner, i.e., stored or, preferably, returned to the acid-producing step.

The percentage of the total feed to the column which is removed from the bottom of the column and passed through the cation exchange column may vary from about 1% to about 5% by weight of the total feed but preferably is maintained as low as possible, that is, from about 1% to 2% by weight of the total feed.

In the cation exchange column any alkaline iodide, such as potassium iodide, for example, as well as any metal iodides generated by corrosion in the system are removed. The cation exchange resin employed in this column is employed in its hydrogen form and is preferably of the strong-acid type although weak-acid type resins can also be used. Both types are readily available as commercial products. Strong-acid cation exchange resins are constituted predominantly of sulfonated styrene-divinylbenzene copolymers although some of the available resins of this type are phenolformaldehyde condensation polymers. The weak-acid cation exchange resins are mostly copolymers of acrylic or methacrylic acids or esters or the corresponding nitriles but a few of those marketed are phenolic resins. Either the gel-type or the macroreticular type resin is suitable but the latter is preferred since organic components are present in the catalyst solution being treated.

The ion exchange treatment can be effected at temperatures anywhere in the range from about 0° to about 120° C although lower or higher temperatures limited only by the stability of the resin can be employed. However, preferred temperatures are those in the range from about 20° to about 50° C since more effective removal of any corrosion metals present is achieved at the higher temperatures. If temperatures above the boiling point of the bottoms stream are employed, then operation under pressure will be required to maintain the stream in the liquid phase. However, pressure is not a critical variable. Generally, atmospheric pressure or a pressure slightly above atmospheric is employed but superatmospheric or subatmospheric pressure can be used if desired.

The rate of flow of the bottoms stream through the resin will, in general, be that recommended by the resin manufacturer and will usually be from about 1 to about 20 bed volumes per hour. Preferably, the flow rates are kept to from about 2 to about 12 bed volumes per hour. After it has become exhausted, i.e., when the metal from the alkaline treating agent and/or corrosion products are breaking through into the effluent, the flow can be switched to a fresh resin bed while the exhausted resin is regenerated. Regeneration of the resin bed is effected by passing through it a solution of a mineral acid such as sulfuric, hydrochloric, phosphoric, hydriodic, and the like. Generally, the acid used in the acid-treating cycle has a concentration in the range from about 10% to about 50%. Quantities employed and procedures are those well established in the art and recommended by the resin manufacturers. Aqueous hydrogen iodide is preferred as a regenerating agent since this acid is normally employed in the reaction system and is readily available for use. Additionally, it has the advantage that its use precludes any contamination of the catalyst solution which after the ion exchange treatment is recycled to the reactor. A still further advantage is that its use eliminates the rinsing step normally required after the regeneration process when other acid regenerants are employed. Solutions of aqueous hydrogen iodide ranging from about 10% to about 57% can be used but those containing about 20% are preferred.

The effluent from the ion exchange column consisting essentially of propionic acid can be recycled to the acid-producing step or to the feed to the distillation zone.

The product stream of essentially dry, purified propionic acid containing less than 20 ppb iodine is removed as a vapor from the lower quarter and preferably from the lower one-tenth of the distillation zone and even more desirably from just above the bottom tray in the distillation zone. The amount of this stream withdrawn in proportion to the total feed is maintained as high as possible consistent with the amounts of the feed removed overhead and via the liquid sidedraw and bottoms.

The purification process of the present invention can be operated on a batch or a continuous basis but continuous operation is preferred.

As will be recognized, various equipment such as pumps, compressors, reboilers, etc., normally employed in carrying out chemical distillation processes can be employed in the process herein. Since these do not form part of the invention details of their use in various phases of the process description have not been included. The invention is illustrated in the following example which, however, is not to be construed as limiting it in any manner whatsoever. All parts given are by weight unless otherwise specified.

EXAMPLE

A stream of crude propionic acid containing 1272 parts of propionic acid, 814 parts of ethyl iodide, 448 parts of water, 48 parts ethyl propionate, 3 parts of hydrogen iodide and 1 part of ethanol is obtained by reacting ethylene, water and carbon monoxide in contact with a catalyst comprising the complex reaction product obtained by combining a rhodium component and an iodine component in the presence of carbon monoxide and flashing overhead of the reaction effluent. This stream is dried and purified in a purification system as illustrated in FIG. 1. The stream at a temperature of around 110° C is introduced at the 22nd plate of a 30-plate distillation column. A stream containing 0.23 part of potassium hydroxide is introduced into the distillation column at the 5th plate. A stream containing approximately 808 parts of ethyl iodide, 422 parts water, 211 parts propionic acid, 47 parts ethyl propionate and 1 part ethanol is removed overhead from the column and condensed, a small part thereof being returned to the column as reflux and the remainder withdrawn for recycle to the acid-producing step. A liquid sidedraw containing about 135 parts propionic acid, 27 parts water, 6 parts ethyl iodide, 3 parts hydrogen iodide, 1 part ethyl propionate and no ethanol is removed from the 21st plate of the column and directed into the condensed overhead stream for storage or recycle as the case may be. A stream containing about 890 parts of propionic acid and less than 20 ppb total iodine is removed as a vapor from the first tray above the bottom of the column.

A stream from the bottom of the column is introduced into a column packed with a strong-acid cation exchange resin manufactured and sold under trademark "Amberlyst 15" by Rohm and Haas Company maintained at a temperature of about 40° and passed down through the resin at a rate of 2 to 4 bed volumes per hour. A stream containing 38 parts propionic acid is recovered as the effluent from the resin bed which is substantially free of potassium, iron and nickel.

What is claimed is:

1. A method for purifying a crude propionic acid stream containing water and iodine either as $I^-$, free iodine, ethyl iodide or all of these as contaminants which comprises:
   1. introducing said stream into the upper section of a distillation zone,
   2. introducing an alkaline compound selected from the group consisting of alkaline compounds of the alkali metals and the alkaline earth metals into the lower third of said distillation zone;
   3. removing overhead from said distillation zone a stream containing the major portion of the water present along with substantially all of the ethyl iodide;
   4. removing as a liquid sidestream from the upper section of said distillation zone all of the hydrogen iodide together with the remaining portion of water;
   5. withdrawing as a vapor near the bottom of said distillation zone the product propionic acid stream containing less than 20 ppb of iodine;
   6. removing a bottoms stream from said distillation zone containing propionic acid, said alkaline compound and metal corrosion products; and
   7. passing said bottoms stream through a cation exchange resin and recovering the effluent from said exchange free of said alkaline compound and said metal corrosion products.

2. The process of claim 1 wherein said distillation zone comprises a distillation column having from about 20 to about 80 theoretical trays.

3. The process of claim 2 wherein said crude propionic acid is introduced into the upper one-third of said distillation column.

4. The process of claim 3 wherein said alkaline compound is introduced into the lower third of said column.

5. The process of claim 4 wherein said alkaline compound is a compound of potassium.

6. The process of claim 5 wherein said potassium compound is potassium hydroxide.

7. The process of claim 6 wherein the overhead fraction from said column constitutes from about 30 to about 70% by weight of the total feed to said column.

8. The process of claim 7 wherein said liquid sidedraw from said column constitutes from about 4 to about 10% by weight of the total feed to said column.

9. The process of claim 8 wherein said bottoms stream from said distillation column constitutes from about 1% to about 5% by weight of the total feed to said column.

10. The process of claim 9 wherein said cation exchange resin is a strong-acid cation exchange resin.

* * * * *